US008752702B2

(12) United States Patent  
Arnett

(10) Patent No.: US 8,752,702 B2  
(45) Date of Patent: Jun. 17, 2014

(54) STERILE BANDAGE WRAPPERS

(76) Inventor: Jaime Arnett, Fishers, IN (US)

(*) Notice: Subject to any disclaimer, the term of this patent is extended or adjusted under 35 U.S.C. 154(b) by 115 days.

(21) Appl. No.: 13/396,035

(22) Filed: Feb. 14, 2012

(65) Prior Publication Data

US 2012/0205275 A1 Aug. 16, 2012

Related U.S. Application Data

(60) Provisional application No. 61/443,317, filed on Feb. 16, 2011.

(51) Int. Cl.
A61B 17/06 (2006.01)
(52) U.S. Cl.
USPC .......................................................... 206/441
(58) Field of Classification Search
CPC ...................................................... A61F 15/001
USPC ..................................... 206/441, 440; 602/57
See application file for complete search history.

(56) References Cited

U.S. PATENT DOCUMENTS

| 2,172,455 A | 9/1939 | Samuel |
| 2,245,738 A | 6/1941 | Taylor |
| 2,880,863 A | 4/1959 | Stanton |
| 2,889,039 A | 6/1959 | Schladermundt et al. |
| 2,897,961 A | 8/1959 | Bush |
| 2,927,689 A | 3/1960 | Look, Jr. |
| 3,007,571 A | 11/1961 | Marinaro |
| 3,018,881 A | 1/1962 | Wall |
| 3,620,441 A | 11/1971 | Robbins |
| 3,899,077 A | 8/1975 | Spiegelberg |
| 4,116,338 A | 9/1978 | Weichselbaum |
| 4,235,337 A | 11/1980 | Dotta |
| 4,264,008 A | 4/1981 | Kozlow |
| 4,418,822 A | 12/1983 | Dotta |
| 4,549,653 A | 10/1985 | Lauritzen |
| 4,997,092 A | 3/1991 | Dupont |
| 5,275,284 A | 1/1994 | Onotsky |
| 5,397,297 A | 3/1995 | Hunter |
| 5,643,188 A | 7/1997 | Oliveira |
| 6,010,002 A | 1/2000 | Petterson |
| 6,053,318 A | 4/2000 | Petterson |
| 6,573,421 B1 | 6/2003 | Lemaire |
| 6,719,137 B2 | 4/2004 | Dotta |
| 6,855,861 B2 | 2/2005 | Dotta |
| 6,923,320 B2 | 8/2005 | Grossman |
| 7,591,371 B2 | 9/2009 | Auger |

FOREIGN PATENT DOCUMENTS

GB 2131299 A * 6/1984 .............. A61F 13/02

* cited by examiner

Primary Examiner — David Fidei  
(74) Attorney, Agent, or Firm — Law Office of Leo Zucker

(57) ABSTRACT

One embodiment of the present disclosure may be directed to a wrapped bandage. The wrapped bandage may include a wrapper having a top portion and a bottom portion. The top portion and the bottom portion each may include a first longitudinal edge, a second longitudinal edge, a third edge, and a fourth edge. Each edge may be continuous and straight along its entire length. The wrapped bandage may also include a bandage including an adhesive area and a pad. The wrapped bandage may also include a cover covering the adhesive area and a portion of the pad. The wrapper may surround the bandage and the cover. The edges of the top portion may be sealed to the edges of the bottom portion providing substantially no separation between the edges of the top and bottom portions.

5 Claims, 25 Drawing Sheets

——— PACKAGE / WRAPPER

— — PROTECTIVE COVERS

------ BANDAGE

FIG. 10
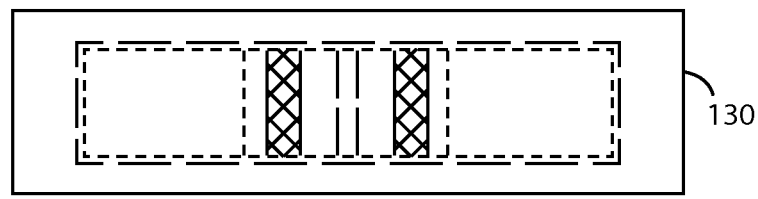
——— PACKAGE / WRAPPER
— — PROTECTIVE COVERS
------ BANDAGE
 BOND AREA
FIG. 11
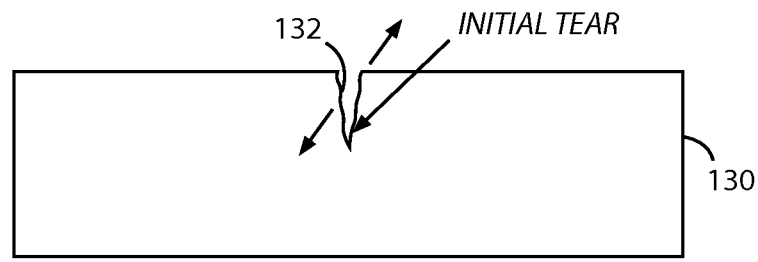

FIG. 19
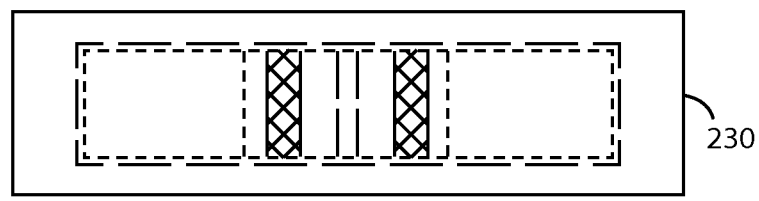
——————— PACKAGE / WRAPPER
— — PROTECTIVE COVERS
- - - - - - BANDAGE
 BOND AREA
FIG. 20
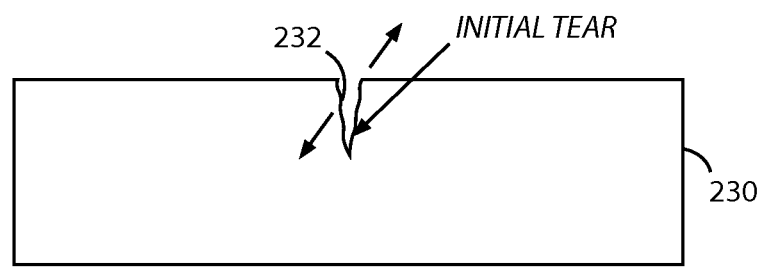

——— PACKAGE / WRAPPER

— — PROTECTIVE COVERS

------ BANDAGE

COVER PEELING BACK

MATERIAL REMOVED TO FORM NOTCHES

STERILE BANDAGE WRAPPERS

CROSS-REFERENCE TO RELATED APPLICATIONS

This application claims the benefit of priority based on U.S. Provisional Patent Application No. 61/443,317, filed Feb. 16, 2011, which is incorporated herein by reference.

FIELD OF THE DISCLOSURE

The present disclosure relates generally to adhesive bandages. The present disclosure also relates generally to a method of manufacturing and using adhesive bandages.

BACKGROUND OF THE DISCLOSURE

Adhesive bandages are frequently used for covering skin wounds. The bandages are usually packaged in paper wrappers and are removed by separating portions of the wrapper that overlie both major sides of the bandage after removing tabs at the ends of the wrapper and/or pulling a tear string. An embodiment of such a bandage wrapper is shown in FIG. 1. The bandage 10 is withdrawn from its wrapper 12 by removing end tabs 14a, 14b, and peeling away cover strips 16a, 16b on the bandage 10 to expose a wound dressing pad 18 and pressure sensitive adhesive areas 20a, 20b of the bandage. The removal and preparation of the bandage 10 for application to a wound thus requires the user to have both (a) visual acuity to locate the end tabs 14a, 14b and/or tear string on the wrapper, and (b) manual dexterity to grasp and remove the tabs and to pull a tear string if also provided.

SUMMARY OF THE DISCLOSURE

According to an embodiment of the present disclosure, a sterile bandage wrapper enables the wrapper to be opened, and the bandage to be removed and applied on a cut or wound in appreciably less time than required with the known wrappers and/or a more sterile manner as compared with known wrappers.

Before explaining various embodiments of the present disclosure, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

According to one embodiment of the disclosure, a wrapped bandage includes a wrapper including a top portion and a bottom portion, the top portion and the bottom portion each including a first longitudinal edge with a first end and a second end, a second longitudinal edge with a first end and a second end, a third edge connecting the first end of the first longitudinal edge and the first end of the second longitudinal edge, and a fourth edge connecting the second end of the first longitudinal edge and the second end of the second longitudinal edge, each edge being continuous and straight along its entire length; a bandage including an adhesive area and a pad; and a cover covering the adhesive area and a portion of the pad, the wrapper surrounding the bandage and the cover; and the edges of the top portion are sealed to the edges of the bottom portion providing substantially no separation between the edges of the top and bottom portions.

According to an aspect of this embodiment, a central portion of the first longitudinal edge of the top portion includes a tear mark.

According to another aspect of this embodiment, the wrapper does not include an end peel or pull apart tab.

According to another aspect of this embodiment, the bandage is unfolded, and the cover is unfolded.

According to another aspect of this embodiment, the cover completely covers a surface of the adhesive area.

According to another aspect of this embodiment, the adhesive area is a first adhesive area and the cover is a first cover, and the bandage includes a second adhesive area, the wrapped bandage includes a second cover covering the second adhesive area and a portion of the pad.

According to another aspect of this embodiment, the first cover and the second cover do not overlap with one another.

According to second embodiment of the present disclosure, a wrapped bandage includes a wrapper including longitudinal edge with a first end and a second end, the longitudinal edge being continuous and straight from the first end to the second end; a bandage including an adhesive area and a pad; and a cover covering the adhesive area and a portion of the pad, the cover including a surface facing the wrapper and includes a portion bonded to the wrapper; the wrapper surrounding the bandage and the cover.

According to an aspect of this embodiment, a central portion of the longitudinal edge includes a tear mark.

According to another aspect of this embodiment, the bandage is unfolded, and the cover is unfolded.

According to another aspect of this embodiment, the cover completely covers a surface of the adhesive area.

According to another aspect of this embodiment, the adhesive area is a first adhesive area and the cover is a first cover, the bandage includes a second adhesive area, the wrapped bandage includes a second cover covering the second adhesive area and a portion of the pad, and the second cover includes a surface facing the wrapper and including a portion bonded to the wrapper.

According to another aspect of this embodiment, the covers do not overlap with one another.

According to another aspect of this embodiment, the portion of the cover bonded to the wrapper extends from a first edge of the cover to a second edge of the cover.

According to a third embodiment of the present disclosure, a wrapped bandage includes a wrapper having a top portion and a bottom portion, the top portion and the bottom portion being unfolded; a bandage including an adhesive area and a pad, and a cover including a cover portion, a fold, a folded portion, and an adhesive portion, the cover portion covers the adhesive area and a portion of the pad, the folded portion is sandwiched between the wrapper and the cover portion, and the adhesive portion is located on a surface of the folded portion facing the wrapper, the adhesive portion being bonded to the wrapper.

According to an aspect of this embodiment, the adhesive portion is located on an end of the folded portion.

According to another aspect of this embodiment, the adhesive portion extends from a first edge of the folded portion to a second edge of the folded portion.

According to another aspect of this embodiment, the adhesive area is a first adhesive area and the cover is a first cover; the cover portion is a first cover portion, the fold is a first fold, the folded portion is a first folded portion, and the adhesive portion is a first adhesive portion; and the bandage includes a second adhesive area, and the wrapped bandage includes a second cover including a second cover portion, a second fold, a second folded portion, and a second adhesive portion, the second cover portion covers the second adhesive area and a portion of the pad, the second folded portion is sandwiched between the wrapper and the second cover portion, and the second adhesive portion is located on a surface of the second folded portion facing the wrapper, the second adhesive portion being bonded to the wrapper.

According to another aspect of this embodiment, the first folded portion and the second folded portion overlap with each other over the pad.

According to another aspect of this embodiment, the wrapper includes a longitudinal edge with a first end and a second end, the longitudinal edge being continuous and straight from the first end to the second end; and the wrapper surrounds the bandage and the cover.

According to another aspect of this embodiment, a central portion of the wrapper does not include a crosswise bond.

According to another aspect of this embodiment, a longitudinal edge of the wrapper includes one of a tear mark, a slit, and a notch.

According to a fourth embodiment of the present disclosure, a wrapped bandage includes a wrapper including a longitudinal edge with a first end and a second end, the longitudinal edge being continuous and straight from the first end to the second end; a bandage including a first adhesive area, a second adhesive area, and a pad; and a first cover and a second cover of approximately the same length, the first cover covers the first adhesive area and a portion of the pad and the second cover covers the second adhesive area and a portion of the pad; the first cover includes a first fold and a first folded portion, and the second cover includes a second fold and a second folded portion; an end of the first folded portion furthest from the pad is sandwiched between a top portion of the wrapper and a bottom portion of the wrapper; an end of the second folded portion furthest from the pad is sandwiched between a top portion of the wrapper and a bottom portion of the wrapper; and the wrapper surrounds the bandage, the first cover, and the second cover.

According to an aspect of this embodiment, the first folded portion and the second folded portion overlap with one another over the pad.

According to another aspect of this embodiment, the first cover completely covers a surface of the first adhesive area, and the second cover completely covers a surface of the second adhesive area.

According to another aspect of this embodiment, a central portion of the longitudinal edge includes a tear mark.

The accompanying drawings, which are incorporated in and constitute a part of this specification, illustrate certain embodiments of the disclosure, and together with the description, serve to explain the principles of the disclosure.

As such, those skilled in the art will appreciate that the conception upon which this disclosure is based may readily be utilized as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

FIG. 10 presents a plan view of a bandage wrapper according to the second embodiment of the present disclosure.

FIGS. 11-17 present a method of removing and applying a bandage according to the second embodiment of the present disclosure.

FIG. 19 presents a plan view of a bandage wrapper according to the third embodiment of the present disclosure.

FIGS. 20-26 present a method of removing and applying a bandage according to the third embodiment of the present disclosure.

DETAILED DESCRIPTION OF THE DRAWINGS

Reference will now be made in detail to the present embodiments of the disclosure, and examples of which are illustrated in the accompanying drawings.

Embodiments of the present disclosure relate to adhesive bandages. Adhesive bandages may include, but are not limited to, strip bandages, winged bandages, fingertip bandages, butterfly bandages, knuckle bandages, triangular bandages, tube bandages, compression bandages, elastic bandages, gauze bandages, donut bandages, pressure bandages, sterilstrips, eye bandages, sterile burn sheets, and adhesive tape. Wrappers of the present disclosure also may be used for other steril, wrapped products, including, for example, nasal strips for relieving nasal congestion or any other wound care bandages.

Figure 2:
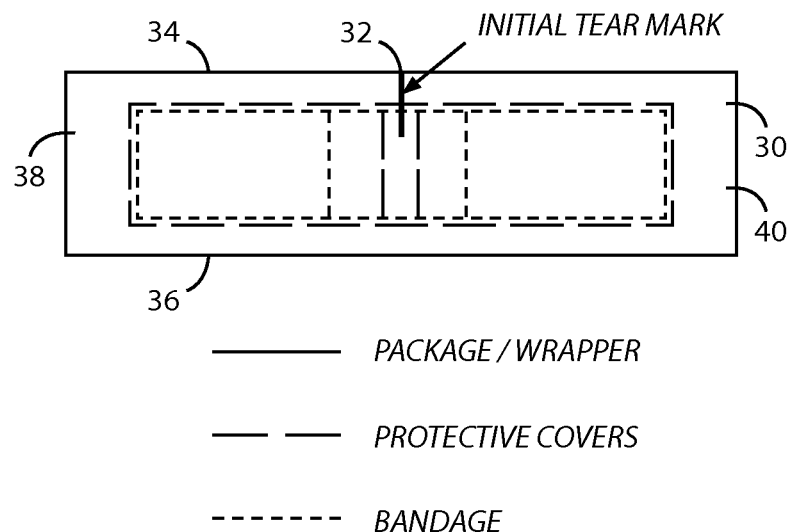
FIG. 2 presents a plan view of a bandage wrapper according to a first embodiment of the present disclosure.

FIGS. 2-8 illustrate one embodiment of the present disclosure. As shown in FIG. 2, a bandage wrapper 30 includes a visible mark or other indicia 32 on the wrapper 30 that is located approximately centrally along one longitudinal edge 34 of the wrapper 30. The mark 32 indicates a position where a user is to make a short tear by hand in preparation for opening the wrapper 30. The bandage wrapper 30 may also include a second longitudinal edge 36 with a first end and a second end, a third edge 38 connecting a first end of the first longitudinal edge 34 and the first end of the second longitudinal edge 36, and a fourth edge 40 connecting the second end of the first longitudinal edge 34 and the second end of the second longitudinal edge 36. Each edge 34, 36, 38, and 40 may be continuous and straight along its entire length. In addition, the bandage wrapper 30 may include a top portion with edges 34, 36, 38, and 40 and a bottom portion with edges 34, 36, 38, and 40. Furthermore, the edges 34, 36, 38, and 40 of the top portion may be sealed to the edges 34, 36, 38, and 40 of the bottom portion allowing for no, or substantially no, separation between the edges 34, 36, 38, and 40 of the top and bottom portions. Accordingly, the bandage wrapper 30 may not include end peels or pull apart tabs, like the tabs known with standard bandage wrappers that are usually about 3-5 millimeters wide.

Figure 3:
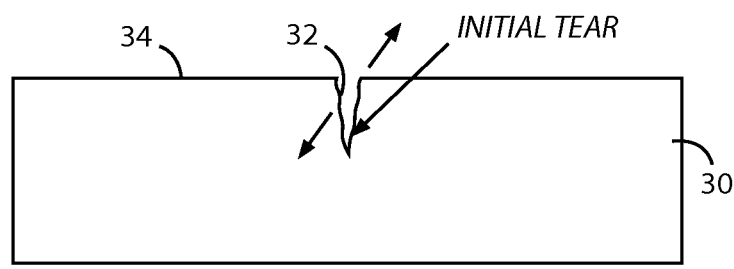
FIGS. 3-8 present a method of removing and applying a bandage according to the first embodiment of the present disclosure.
Figure 4:
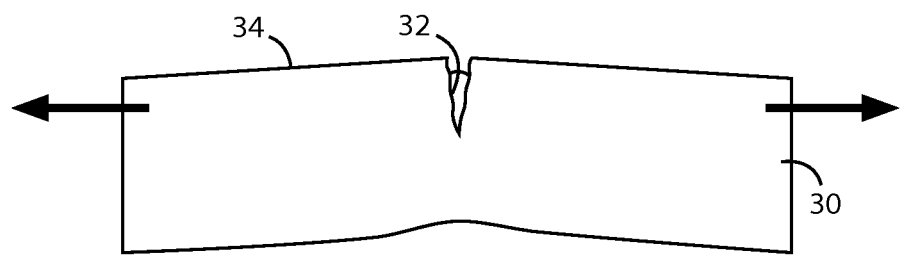
Figure 5:
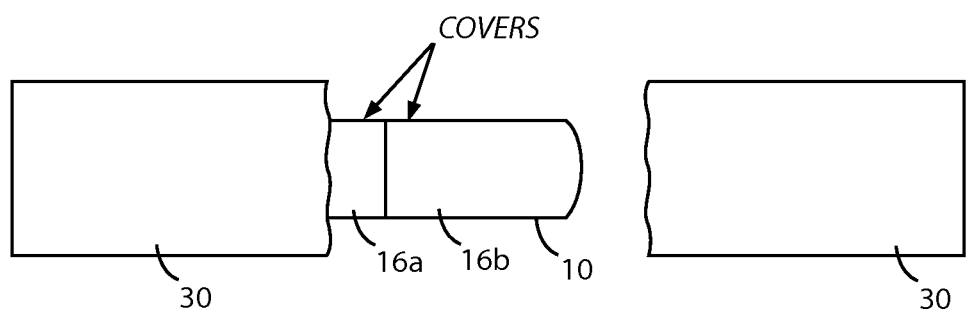
Figure 6:
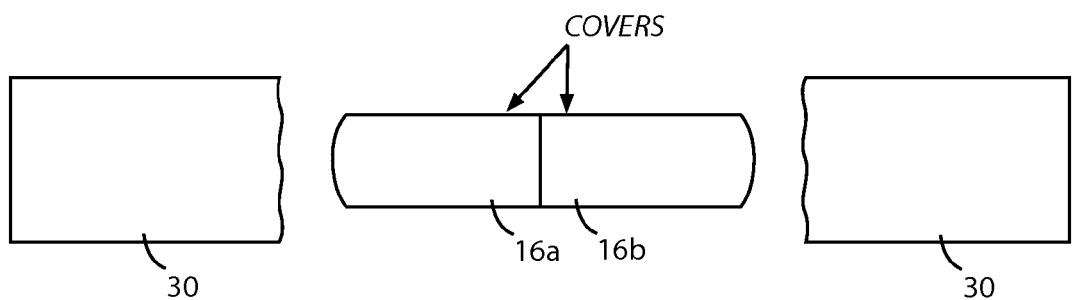
Figure 7:
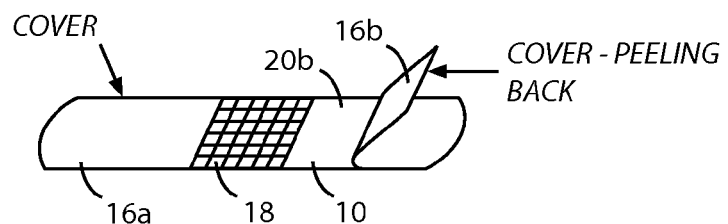
Figure 8:
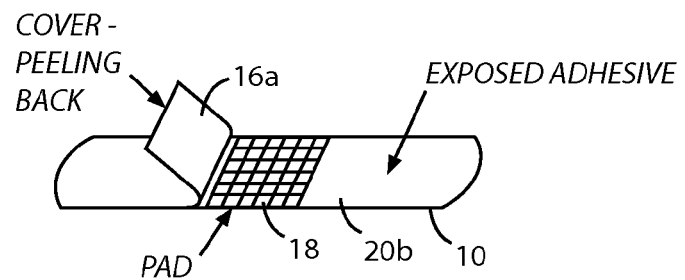

According to another aspect of this embodiment, as shown in FIGS. 3-4, after the tear is made, the bandage wrapper 130 is grasped at opposite ends of the long edge 34 and pulled apart. As shown in FIG. 4, the user may grasp the bandage wrapper 30 beyond the areas covering the bandage 10 in order to avoid pinching the bandage 10 while tension is applied to the wrapper 30. Once the opposite ends of the wrapper 30 are fully separated, as shown in FIGS. 5-6, one end of the bandage 10 is exposed and the rest of the bandage 10 can be removed from the remaining portion of the wrapper 30. As shown in FIGS. 7-8, cover strips 16a, 16b are peeled away to expose the wound dressing pad 18 and the pressure sensitive adhesive areas 20a, 20b of the bandage 10.

Figure 1:
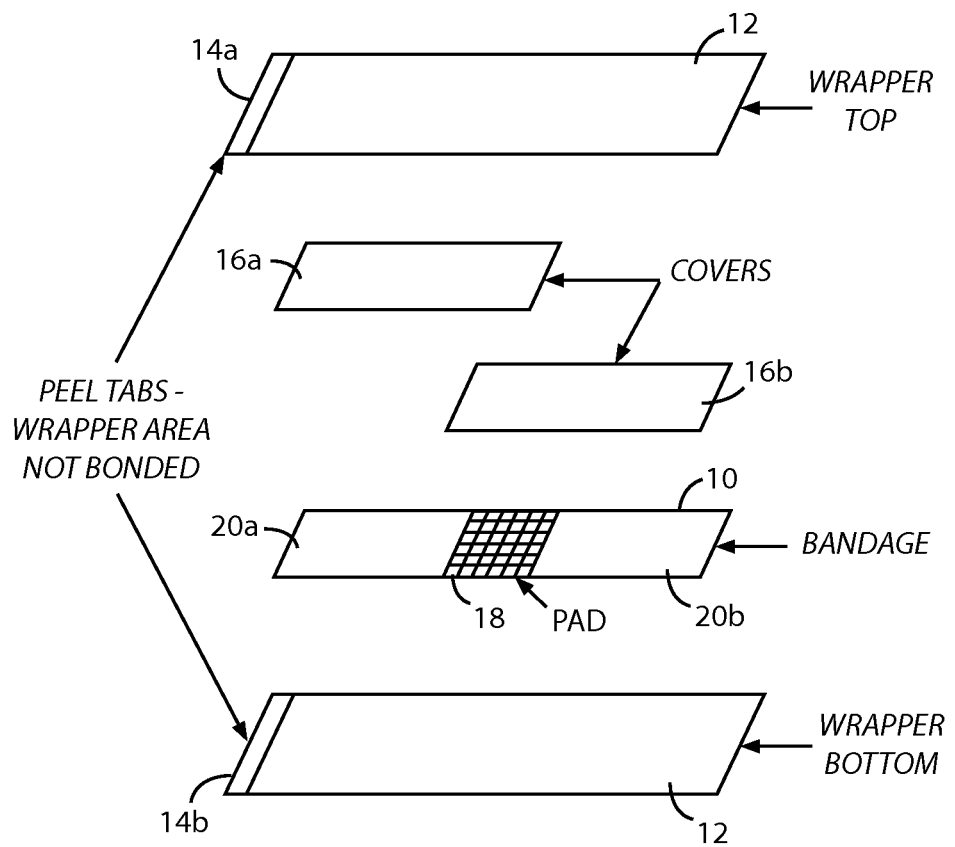
FIG. 1 presents an exploded view of a conventional bandage wrapper.

According to an aspect of this embodiment, after making the short tear by hand at the mark 32, the tension needed to pull apart the bandage wrapper 30 enough to remove the bandage 10 is significantly and unexpectedly less than that required if a slit or notch is pre-cut in the vicinity of the mark 32. The wrapper 30 of FIG. 2 can be manufactured in a manner the same or similar to that used to make the wrapper of FIG. 1, and providing the mark 32 on the wrapper 30 shows the user where he or she should tear the wrapper in order to remove the bandage 10. In addition, the end tabs 14a, 14b on the prior wrapper 12 may be eliminated saving both material and manufacturing costs.

Figure 9:
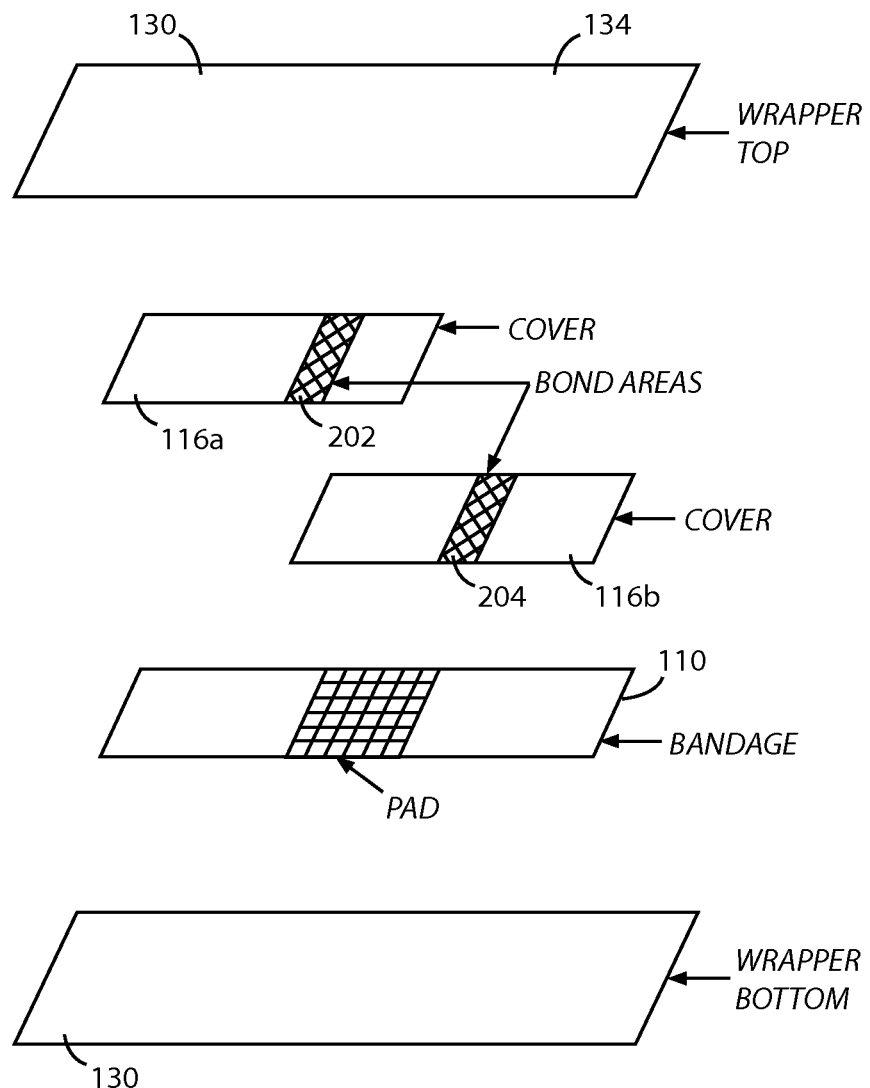
FIG. 9 presents an exploded view of a bandage wrapper according to a second embodiment of the present disclosure.
Figure 12:
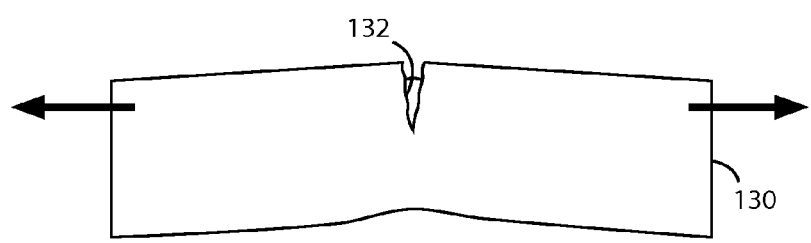

FIGS. 9 to 17 illustrate a second embodiment of the present disclosure. The bandage wrapper 130 includes elements that are the same or similar to elements of the wrapper 30 as shown in FIGS. 2 to 8. As shown in FIGS. 9-11, the wrapper 130 includes a longitudinal edge 134 with a first end and a second end, the longitudinal edge 134 being continuous and straight from the first end to the second end. The wrapper 130 enables the cover strips 116a, 116b to be removed automatically when the wrapper 130 is separated from the bandage 110 after the user makes the initial hand tear at the mark 132. Adhesive bonding areas 202, 204 are provided on outwardly facing surfaces of the cover strips 116a, 116b so that the strips will also adhere to the confronting, inwardly facing surface of the wrapper 130. The bonding areas 202, 204 should be spaced from one another enough to ensure that the wrapper 130 will tear and separate in the region between the bonding areas, and that both cover strips 116a, 116b will peel away from the bandage 110 as the separated portions of the wrapper 130 are removed. The bonding areas 202, 204 may be thin and rectangular shaped. In addition, the bonding areas 202, 204 may extend in a transverse direction across a width of each cover strip 116a, 116b.

The adhesive bond areas 202, 204 of this embodiment may include, for example, pressure-sensitive adhesives (rubbers, acrylate and silicone formulations), dissolvable adhesives, removable adhesives, reactive adhesives, drying adhesives, contact adhesives, light-curing adhesives, thermoplastic adhesives, synthetic adhesives (acrylics, cynoacrylates, silicone, polyurethane), biological adhesives, or any other suitable adhesive known in the art.

Figure 13:
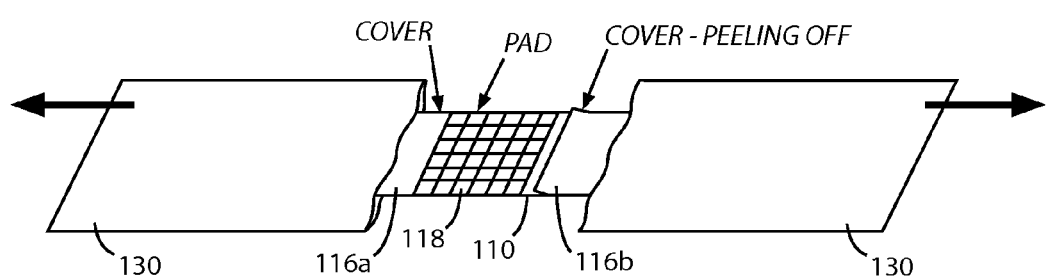
Figure 14:
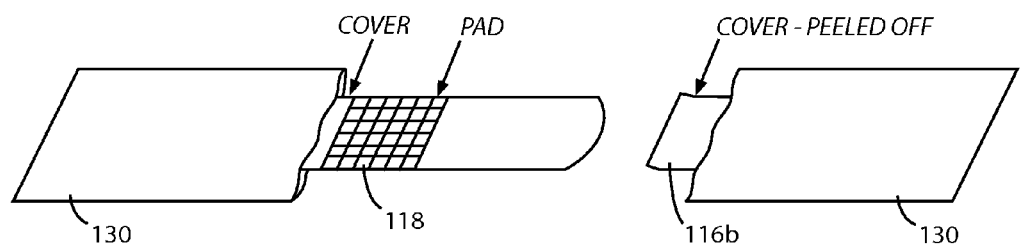
Figure 15:
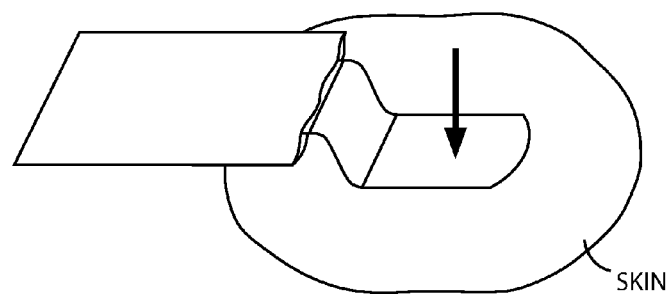
Figure 16:
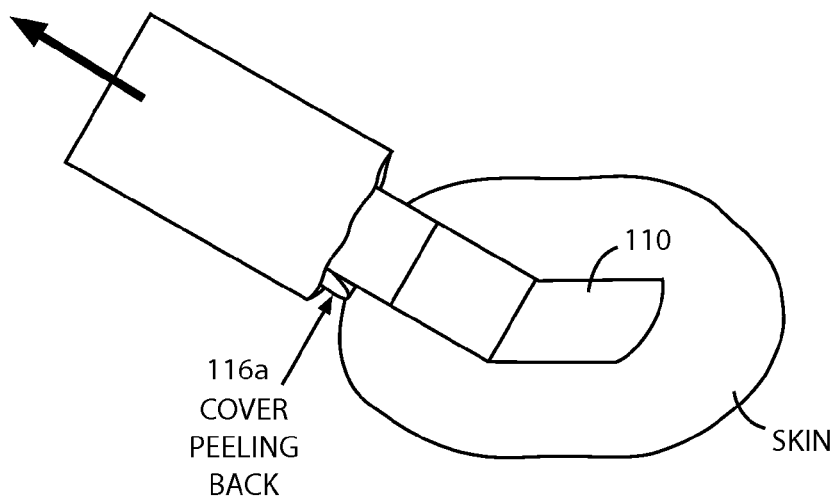
Figure 17:
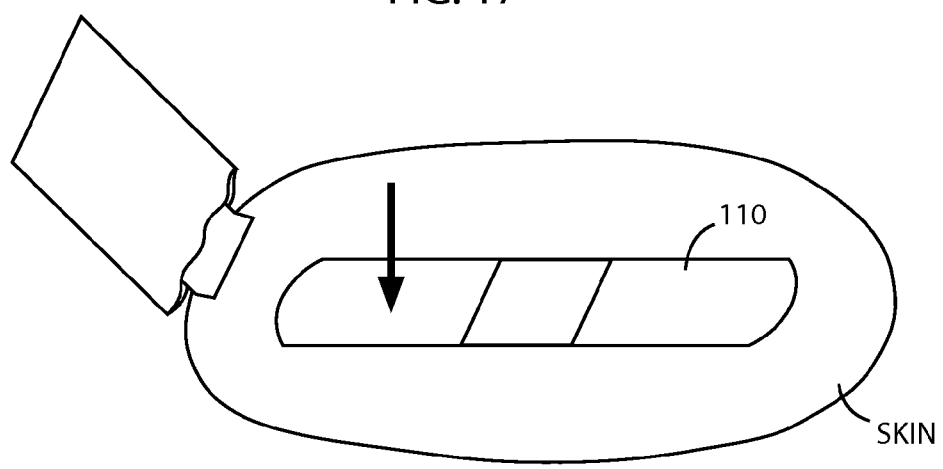

FIG. 10 is a plan view of the bandage wrapper 130 and FIGS. 11 to 17 show a progression of removing the bandage 110 from the wrapper 130 and applying the bandage 110. According to one aspect of this embodiment, as shown in FIG. 13, after a user makes the initial tear, the opposite ends of the wrapper 130 are pulled apart to separate the wrapper 130 into left and right halves. Then, only one half, (e.g., the right half in FIG. 13), is pulled off of the bandage 110 so as to peel the cover strip 116b away from the pressure sensitive part of the right side of the bandage 110. As shown in FIG. 15, with the pressure sensitive adhesive at the right side of the bandage 110 exposed, the user applies the exposed right side of the bandage 110 adjacent to the wound. As shown in FIG. 16, the left half of the wrapper 130 is pulled off of the bandage 110 so as to peel the cover strip 116a away from the pressure sensitive part of the left side of the bandage. As shown in FIG. 17, with the pressure sensitive adhesive at the left side of the bandage 110 exposed, the user applies the wound dressing pad on the wound, and the exposed left side of the bandage 110 is applied adjacent the wound opposite the right side of the bandage. It will be appreciated that with this embodiment, direct contact with the wound by the user is easily avoided over the entire bandage removal and application process, providing for a more sterile application of the bandage.

Figure 18:
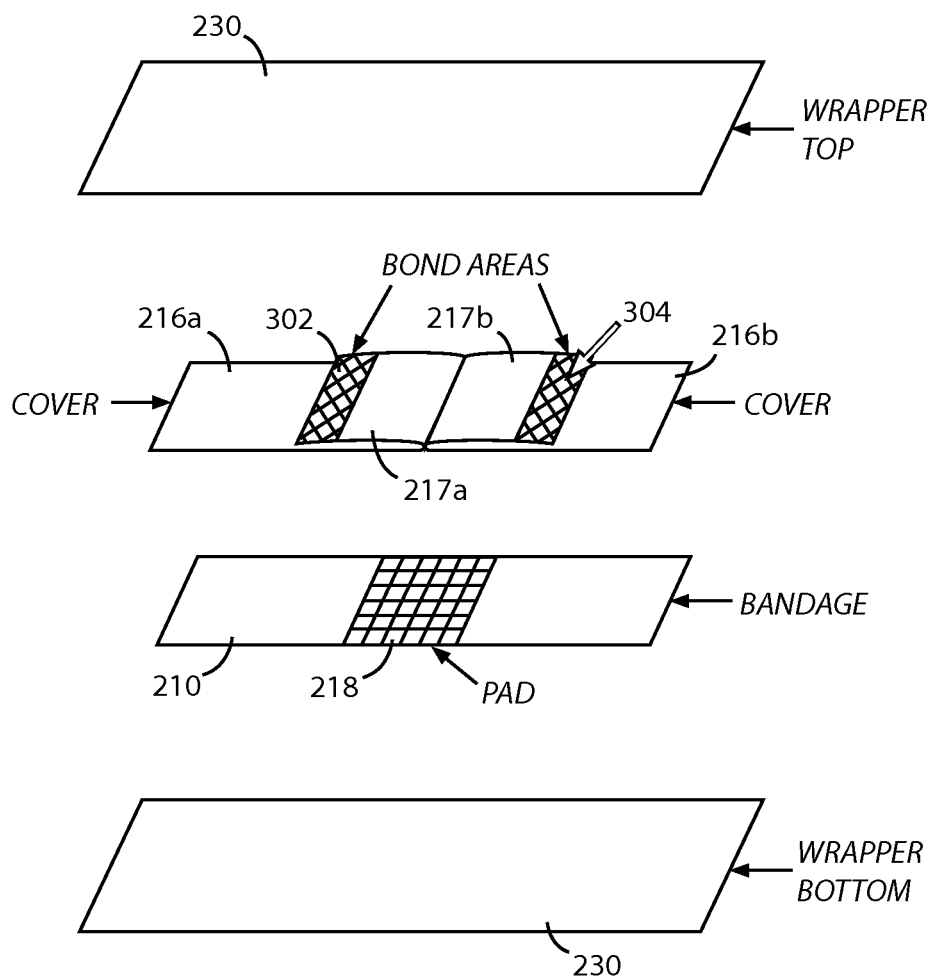
FIG. 18 presents an exploded view of a bandage wrapper according to a third embodiment of the present disclosure.

FIGS. 18 to 26 illustrate a third embodiment of the present disclosure. The bandage wrapper 230 includes elements that are the same or similar to elements of the wrapper 30 as shown in FIGS. 2 to 8. As shown in FIGS. 18 to 19, the wrapper 230 includes a longitudinal edge 234 with a first end and a second end, the longitudinal edge 234 being continuous and straight from the first end to the second end. The wrapper 230 also features automatic removal or peeling away of protective cover strips 216a, 216b as the wrapper is separated from the bandage 210. Each cover strip 216a, 216b has an overlapping folded portion 217a, 217b, and an adhesive bonding area 302, 304 is applied on each of the folded portions 217a, 217b.

In addition to the overlapping folded portion 217a, 217b, and the adhesive bonding area 302, 304, each cover strip 216a, 216b may also include a fold 219a, 219b and a cover portion 220a, 220b, the cover portion 220a, 220b covering the adhesive of the bandage 210 and a portion of the pad 218 of the bandage 210. In addition, the overlapping folded portion 217a, 217b may be sandwiched between the wrapper 230 and the cover portion 220a, 220b.

Accordingly, less force may be needed to separate the left and right halves of the wrapper 230 after making an initial tear and removing the cover strips 216a, 216b, than the force needed to separate the wrapper 130 and remove the cover strips 116a, 116b according to the embodiment shown in FIGS. 9 to 17. As with the second embodiment, there should be enough space between the bonding areas 302, 304 to ensure the wrapper 230 will tear fully between the bonding areas and that both cover strips 216a, 216b will be peeled away as each separated half of the wrapper 230 is withdrawn from the bandage 210. According to an aspect of this embodiment, the bonding areas 302, 304 may be thin and rectangular shaped. In addition, the bonding areas 302, 304 may extend in a transverse direction across a width of each cover strip 216a, 216b. The adhesive bonding areas 302, 304 may be located adjacent an end portion of each folded portion 217a, 217b and located on an upper side of each folded portion 217a, 217b.

According to another aspect of this embodiment, the upper side of each folded portion 217a, 217b is approximately one-half the length of an underside portion of the folded portion 217a, 217b. In addition, the folded portions 217a, 217b may slightly overlap with one another.

The adhesive bond areas 302, 304 of this embodiment may include, for example, pressure-sensitive adhesives (rubbers, acrylate and silicone formulations), dissolvable adhesives, removable adhesives, reactive adhesives, drying adhesives, contact adhesives, light-curing adhesives, thermoplastic adhesives, synthetic adhesives (acrylics, cynoacrylates, silicone, polyurethane), biological adhesives, or any other suitable adhesive known in the art.

It is known in the manufacturing art of some bandages to attach protective cover strips to the adhesive portions of the bandages, and then cut out individual bandages with associated cover strips simultaneously using the same cutting die. The second and third embodiments described above will allow the bandages 110, 210 and their associated cover strips 116a, 116b, and 216a, 216b to be cut by the same die simultaneously helping to save material and manufacturing costs.

Figure 21:
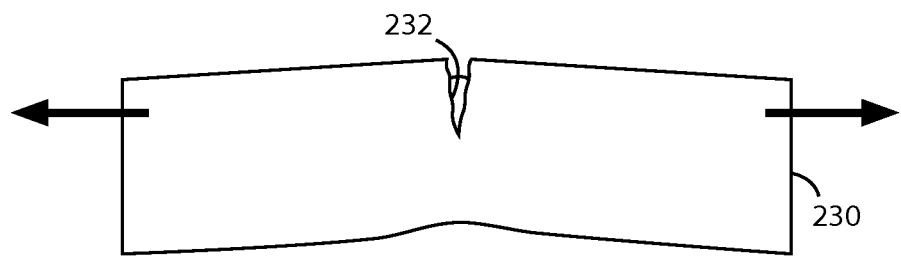
Figure 22:
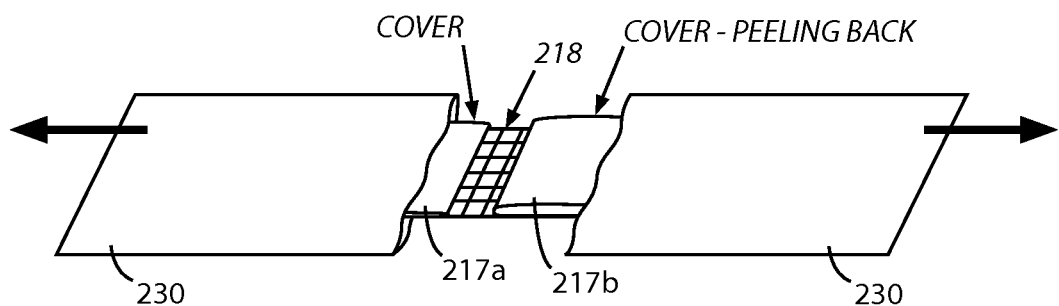
Figure 23:
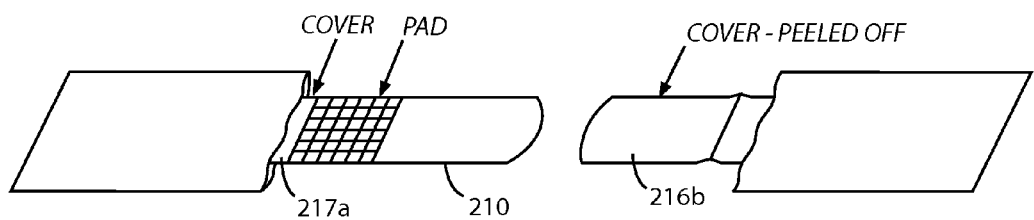
Figure 24:
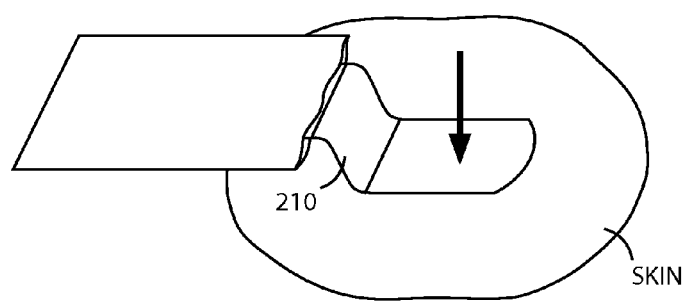
Figure 25:
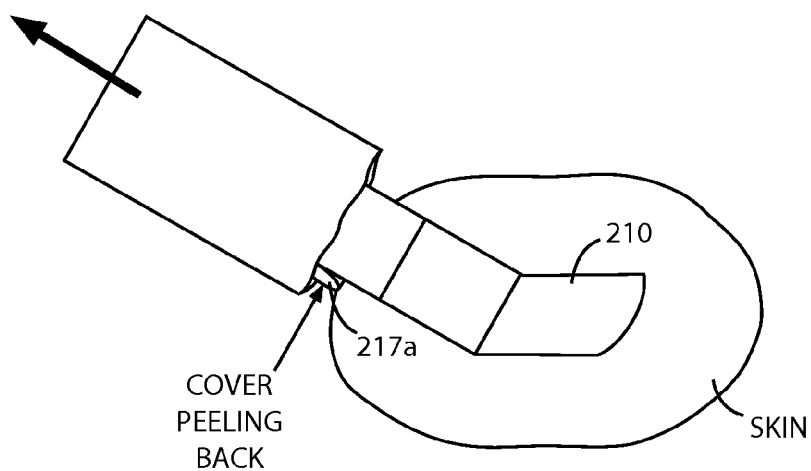
Figure 26:
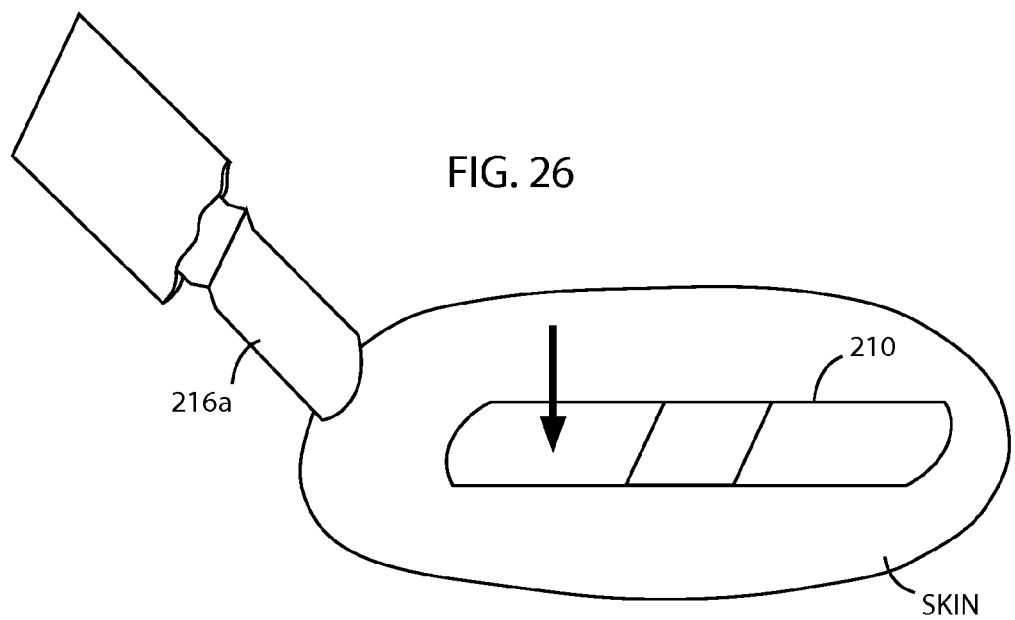

FIGS. 20 to 26 show a progression of opening and applying the bandage 210. According to one aspect of the present embodiment, as shown in FIGS. 21-23, after the wrapper 230 is fully separated, the right half of the wrapper 230 is withdrawn and the protective cover strip 216b at the right side of the bandage 210 peels away to expose the pressure sensitive adhesive of the bandage. As shown in FIG. 24, this allows the user, to apply the exposed (right) side of the bandage 210 adjacent to the wound. As shown in FIGS. 25-26, the left half of the wrapper 230 is then withdrawn from the bandage 210 causing the cover strip 216a at the left side to the bandage to be peeled away, and allowing the user to apply the bandage dressing pad 218 over the wound and the exposed pressure sensitive adhesive of the bandage next to the wound. It will be appreciated that this avoids any direct contact by the user with the wound dressing pad during the entire wrapper removal and bandage application process, providing for a more sterile application of the bandage.

Figure 27:
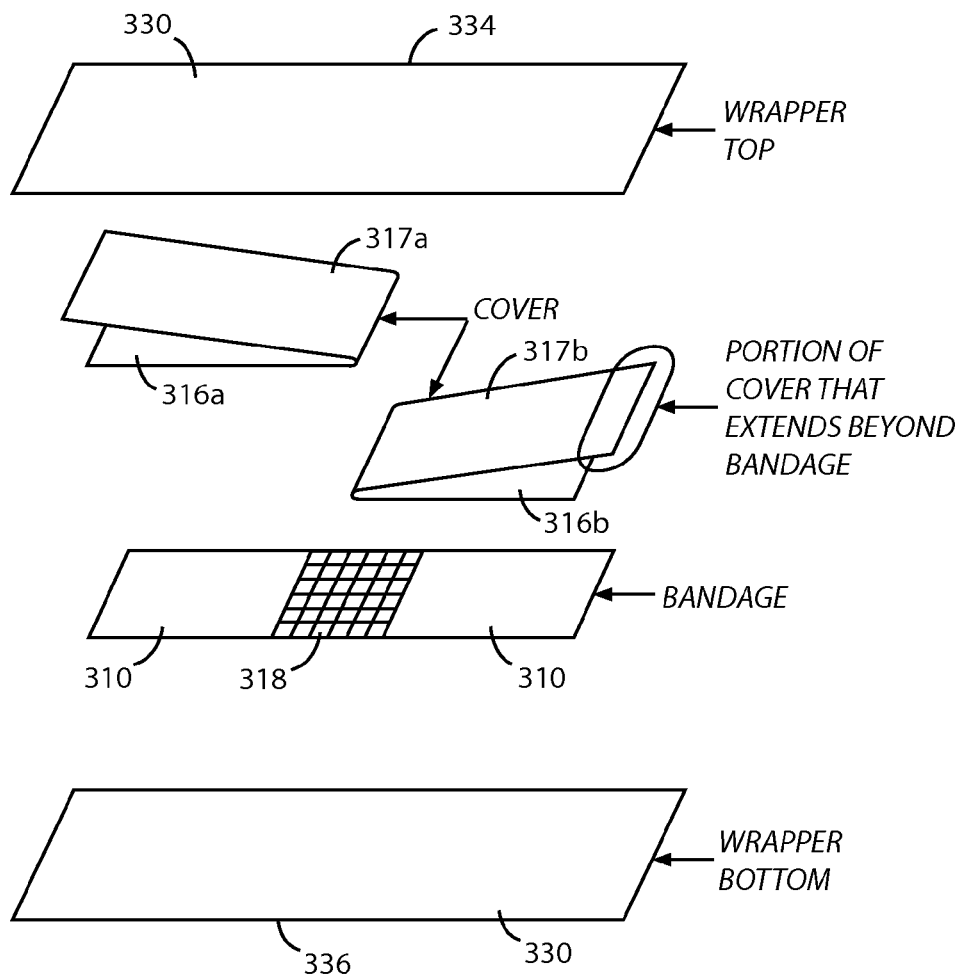
FIG. 27 presents an exploded view of a bandage wrapper according to a fourth embodiment of the present disclosure.
Figure 28:
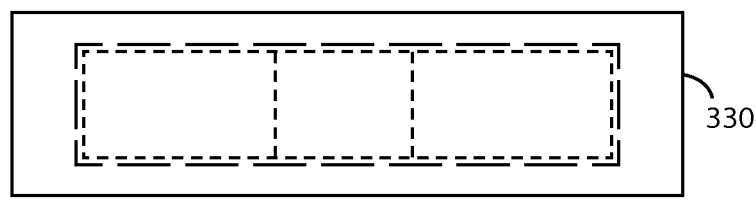
FIG. 28 presents a plan view of a bandage wrapper according to the fourth embodiment of the present disclosure.
Figure 29:
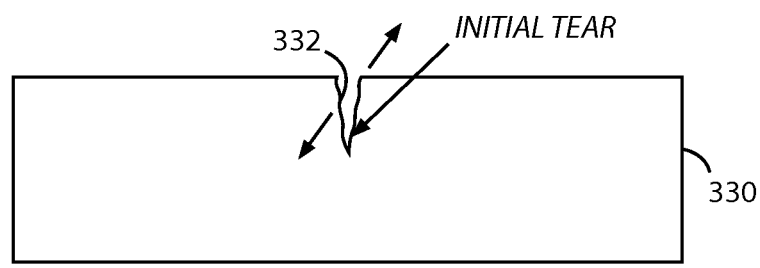
FIGS. 29-35 present a method of removing and applying a bandage according to the fourth embodiment of the present disclosure.
Figure 30:
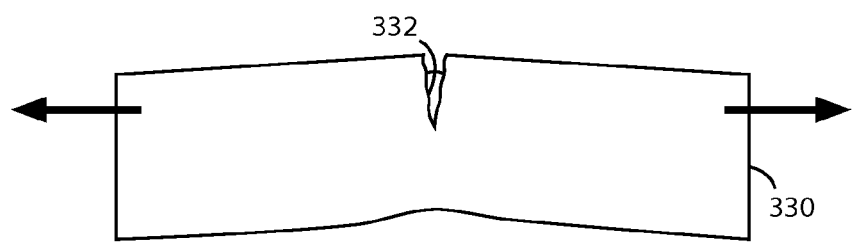
Figure 31:
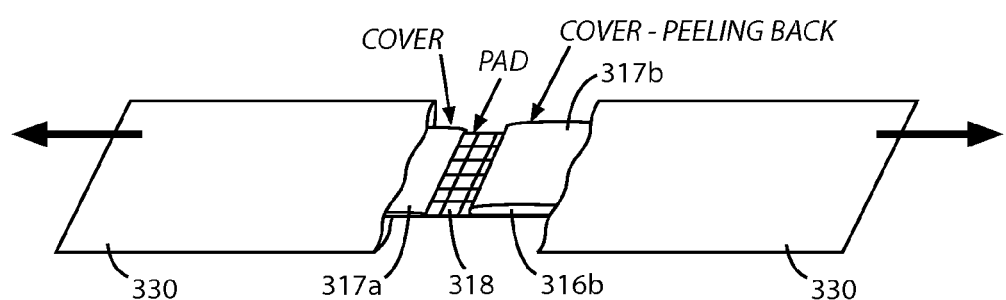
Figure 32:
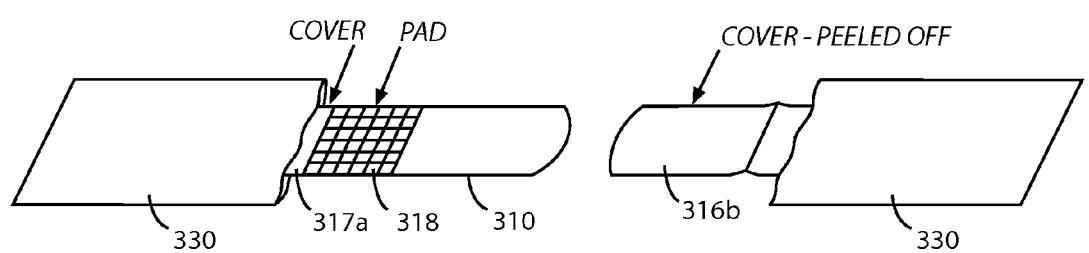
Figure 33:
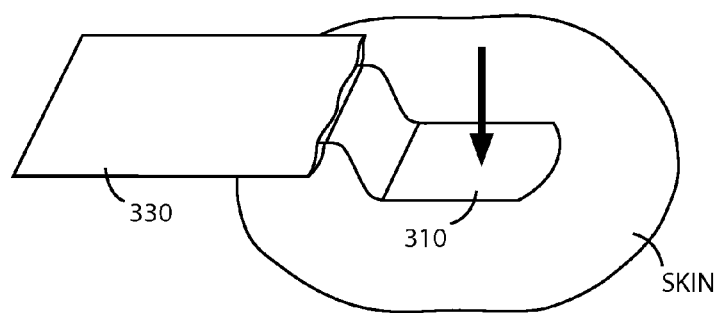

FIGS. 27 to 35 illustrate a fourth embodiment of the present disclosure. The bandage wrapper 330 includes elements that are the same or similar to elements of the wrapper 30 as shown in FIGS. 2 to 8. As shown in FIGS. 27 to 28, wrapper 330 includes a longitudinal edge 334 with a first end and a second end, the longitudinal edge 334 being continuous and straight from the first end to the second end. The wrapper 330 also features automatic removal of protective cover strips 316a, 316b from the pressure sensitive adhesive areas of the bandage 310 when the wrapper 330 is removed. The cover strips 316a, 316b have folded portions 317a, 317b, each folded portion having an end which extends beyond the opposite ends of the adhesive portions of the bandage 310. As the left and right halves of the wrapper 330 are grasped and separated after making the initial tear, the extended ends of the cover strip portions 317a, 317b are pinched between the top and bottom sides of the wrapper 330. As the wrapper 330 is withdrawn from the bandage 310, the cover strips 316a, 316b are peeled from the bandage 310.

Figure 34:
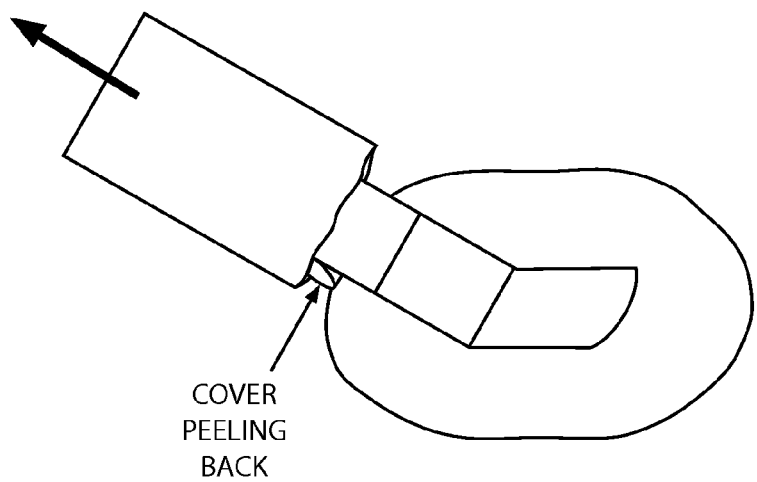
Figure 35:
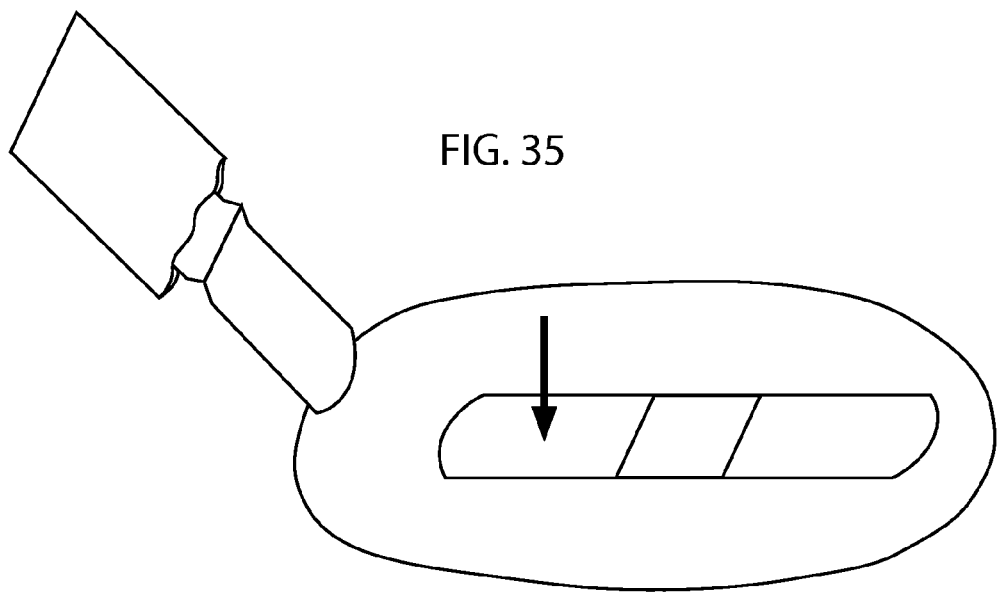

FIGS. 29 to 35 show the progression of opening the wrapper 330 and applying the bandage 310. According to an aspect of this embodiment, as shown in FIG. 30-33, as the right half of the wrapper 330 is removed, the right protective strip 316b automatically peels away to expose the pressure sensitive adhesive on the right side of the bandage. It will be appreciated that this allows the user to apply the exposed right side of the bandage adjacent to the wound area. As shown in FIGS. 34-35, the left half of the wrapper is then removed, allowing the user to apply the wound dressing pad over the wound and the exposed left side of the bandage next to the wound area. It will be appreciated with this embodiment, the user also avoids direct contact with the wound dressing pad during this process, providing for a more sterile application of the bandage.

According to another embodiment of the present disclosure, instead of requiring the user to make an initial tear at a pre-printed tear mark or other indicia on the bandage wrapper, the wrapper may be produced with a pre-cut slit or notch in the same region of the wrapper. While this would eliminate the need for the user to make the initial tear, it would require an additional manufacturing step to cut the slit or notch, and a sufficient area of the wrapper must extend beyond the perimeter of the bandage to ensure that the bandage is properly sealed before use. The slitting or notching step may be incorporated with existing bandage wrapper slitting operations, wherein it is common for bandages to be produced from large sheets which are slit apart to form individual bandages or strips of bandages. For example, FIGS. 36 to 46 show various embodiments of slit and notch arrangements according to the present disclosure.

Figure 36:
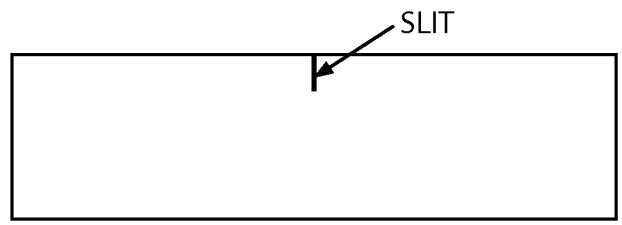
FIGS. 36 to 46 present various embodiments of slit and notch arrangements according to the present disclosure.
Figure 37:
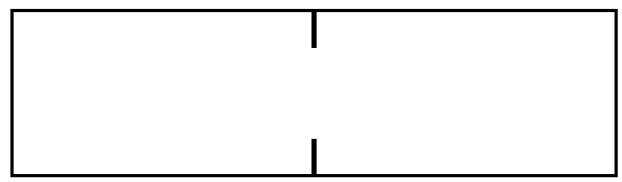
Figure 38:
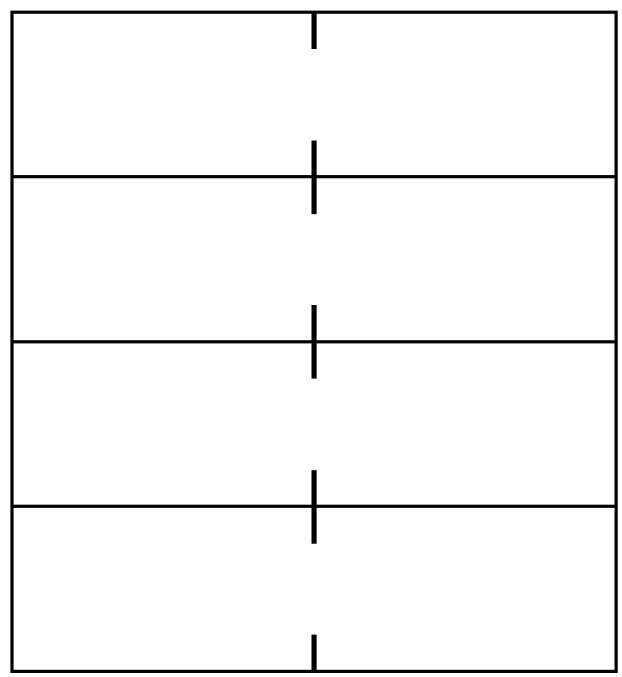

FIGS. 36 to 38 illustrate embodiments of a slit and notch arrangement according to the present disclosure. As shown in FIG. 36, a first slit may be located in a central location of the bandage wrapper and extend in a downward transverse direction from a top edge across a portion of the width of the bandage wrapper. As shown in FIGS. 37-38, the bandage wrapper may include a second slit located opposite the first slit. The second slit may extend in an upward transverse direction from a bottom edge across a portion of the width of the bandage wrapper.

Figure 39:
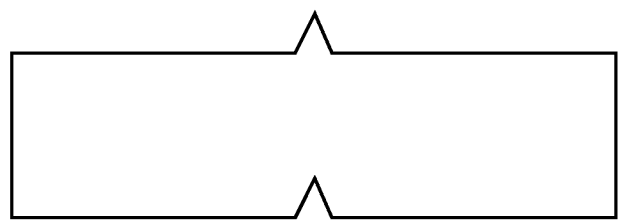
Figure 40:
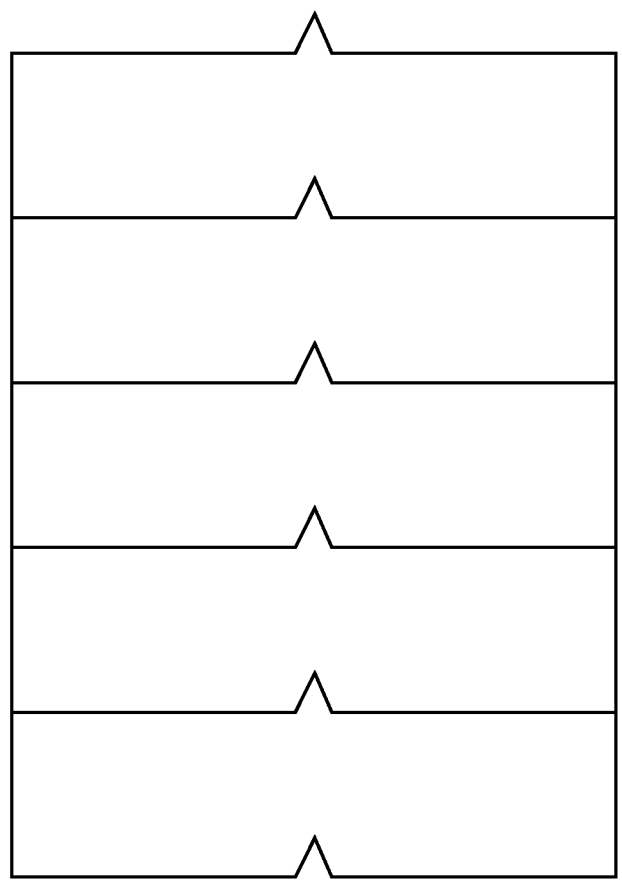

FIGS. 39 to 40 illustrate further embodiments of a slit and notch arrangement according to the present disclosure. As shown in FIGS. 39 to 40, the slit or notch may include a triangular protrusion at a top edge of the bandage wrapper and a triangular notch located at the bottom edge of the bandage wrapper.

Figure 41:
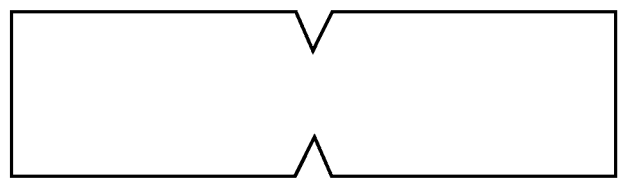
Figure 42:
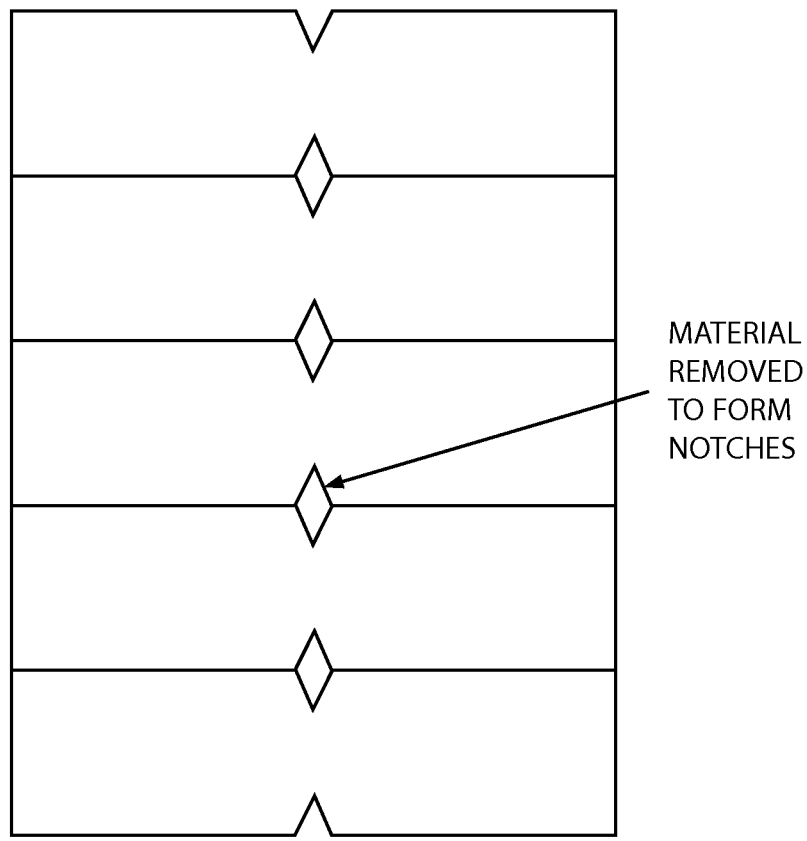

FIGS. 41 to 42 illustrate still further embodiments of a slit and notch arrangement according to the present disclosure. As shown in FIGS. 41 to 42, the slit or notch may include an inwardly protruding triangular shaped notch at a top edge of the bandage wrapper and an inwardly protruding triangular shaped notch located at the bottom edge of the bandage wrapper.

Figure 43:
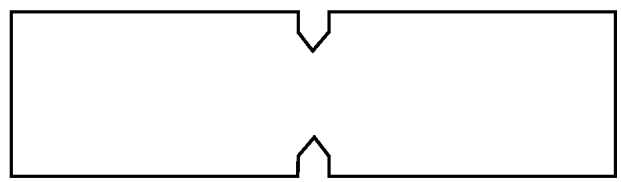
Figure 44:
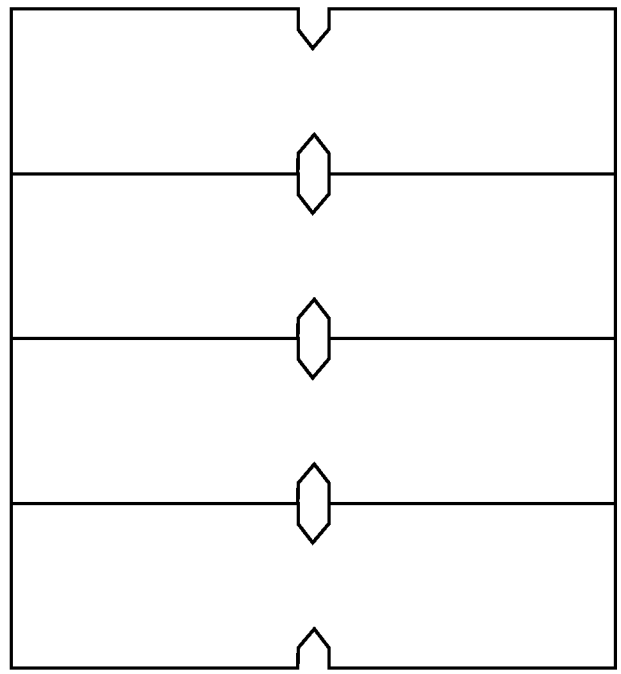
Figure 45:
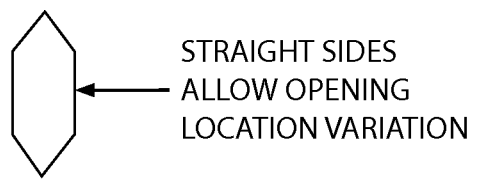

FIGS. 43 to 44 illustrate still further embodiments of a slit and notch arrangement according to the present disclosure. As shown in FIGS. 43 to 44, the slit or notch may include an inwardly protruding half diamond shaped notch, including two straight sides, at a top edge of the bandage wrapper and an inwardly protruding half diamond shaped notch, including two straight sides, located at the bottom edge of the bandage wrapper.

Figure 46:
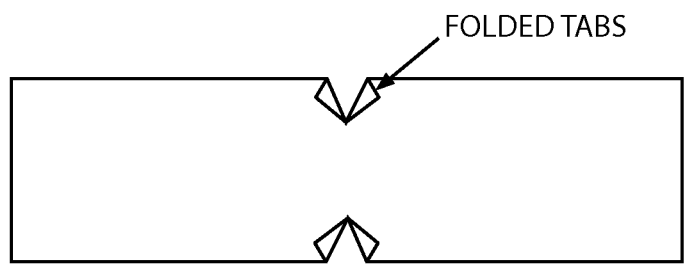

FIG. 46 illustrates another embodiment of a slit and notch arrangement according to the present disclosure. As shown in FIG. 46, the slit or notch may include an inwardly protruding notch, with folded tabs, at a top edge of the bandage wrapper and an inwardly protruding notch, including folded tabs, located at the bottom edge of the bandage wrapper.

Simple graphics are typically printed on bandage wrappers or packaging to illustrate how the wrappers are to be removed. According to various embodiments of the present disclosure, various graphics can also be printed or displayed on the bandage wrappers in order to convey corresponding instructions for opening the wrappers. For example, as shown in FIG. 11, a "tear" graphic may be printed at the location on the wrapper where the user makes the initial tear.

The disclosed embodiments of the present disclosure may be produced using the same or similar methods as currently used in the manufacture of wrapped sterile bandages. That is, no major modifications or replacement of existing manufacturing equipment is required. Having the user make the initial tear allows the wrapper to remain the same size as existing bandage wrappers, so that no additional wrapper material need be consumed beyond that used in the production of the existing bandage wrappers.

According to various embodiments of the present disclosure, the following advantages are also obtained by having the user make the initial tear by hand, rather than providing the wrapper with a pre-cut tear or notch.

1. Less outer wrapper material is required for the hand tear wrapper. Since the perimeter of the wrapper must be sealed to maintain sterility of the bandage, more wrapper material would be needed if the width of the sealed region is to be maintained.

2. A precise cut would be needed in production so that the cut does not encroach into the sealed region of the wrapper, and the cut penetrates the wrapper material enough to allow the user to start to separate the wrapper.

3. It has been discovered that the wrapper can be opened and separated using significantly less force when making the initial tear by hand, when compared to the force needed to separate and open a wrapper having a cut (see the data in Tables 1, 2 and 3, below). This allows a larger population to use the inventive wrappers and the bandages contained therein successfully.

In addition, according to various embodiments of the present disclosure, the bandage wrapper does not require use of peel-apart tabs and consequently there will be a savings of material resulting from the elimination of the tabs. This includes the wrapper paper, adhesive and ink. The savings resulting from elimination of the tabs is significant and can range between 5 and 18% depending on the bandage.

Furthermore, for some currently available bandage wrappers, the peel tabs are made by folding over the end of the wrapper strip. According to various embodiments of the present disclosure, this folding operation would also be eliminated.

Also, reducing the amount of materials used benefits the environment by requiring less energy to make the raw materials and reduction of inherent by-products of the manufacturing processes.

In addition, there is a potential savings for the adhesive that is used to attach the wrapper halves. Since the adhesive does not need to be pulled apart, a less expensive adhesive may be suitable.

Also, some current arrangements of bandages and wrappers require tearing the wrapper on one side or the other of the gauze pad instead of near the center of the bandage. If not torn at the pad region near the center of the bandage, some current bandages are susceptible to tearing of the adhesive coated flexible portion of the bandage that is intended to adhere to the skin.

Figure 47:
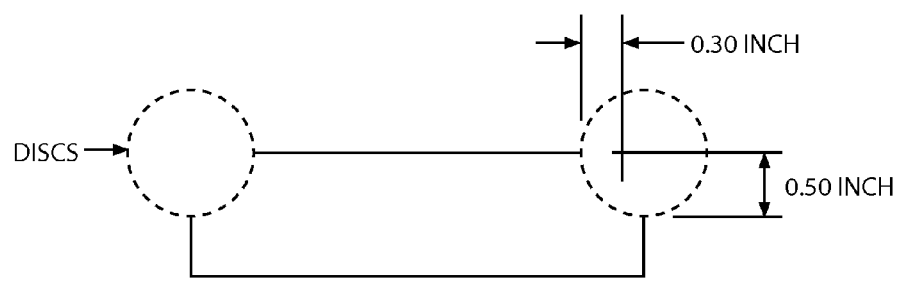
FIGS. 47 to 48 present a method of determining the separation forces needed for bandage wrappers.

Wrapped bandages from three major manufacturers (Band-aid, Nexcare, and Royal) were tested to determine the force required to shear the wrappers apart in order to expose the wrapped bandages. The opposite ends of each wrapper were gripped by elastomer discs to simulate grasping by a user's fingers. FIG. 47 shows the location of the grips, representing the preferred grasping locations.

Figure 48:
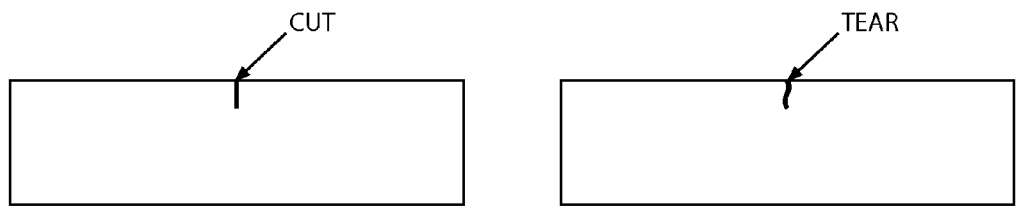

The tests evaluated the separation forces needed for bandage wrappers having a clean cut versus a hand tear to start the wrapper separation. The cuts and the tears were located at the center of one long edge of the bandage. The cut lengths were 1/8 inch and 3/16 inch long, starting at the wrapper edge toward the center of the bandage. The hand tear was made from the wrapper edge and extended to and sometimes slightly past the bandage. As shown in FIG. 48, tearing to the edge of the bandage is a very natural motion.

It is important to note that there is a tradeoff in determining the length of the cut. The cut needs to be long enough to function as a point of stress concentration. Generally, based on additional testing, the longer the cut the easier it is to shear the wrapper. There is also a desire to minimize the length of the cut, however, because the wrapper must increase in width by an amount equal to the length of the cut in order to maintain the sterile seal around the perimeter of the bandage.

TABLE 1

Separation Force testing of "Band-Aid" Brand Bandages

| Model | Size (inch) | Start | Sample size | Average (lbs) | Standard Deviation (lbs) |
| --- | --- | --- | --- | --- | --- |
| Plastic Strip | 3/4 × 3 | 1/8" cut | 30 | 6.1 | 0.91 |
| Plastic Strip | 3/4 × 3 | 3/16" cut | 10 | 4.33 | 0.96 |
| Plastic Strip | 3/4 × 3 | tear | 30 | 2.67 | 0.5 |
| Plastic Strip | 5/8 × 2 1/4 | 1/8" cut | 10 | 6.15 | 0.5 |
| Plastic Strip | 5/8 × 2 1/4 | 3/16" cut | 10 | 5.17 | 0.85 |
| Plastic Strip | 5/8 × 2 1/4 | tear | 10 | 2.68 | 0.41 |
| Sport Strip | 1 × 3 | 3/16" cut | 10 | 5.49 | 0.87 |
| Sport Strip | 1 × 3 | tear | 10 | 3.41 | 0.63 |
| Antibiotic | 3/4 × 3 | 1/8" cut | 10 | 13.4 | 1.1 |
| Antibiotic | 3/4 × 3 | tear | 31 | 6.1 | 0.91 |
| Antibiotic | 5/8 × 2 1/4 | 1/8" cut | 9 | 11.6 | 1.34 |
| Antibiotic | 5/8 × 2 1/4 | tear | 9 | 7.4 | 1.1 |

The overall weighted average for Band-Aid bandages with Tear/Cut 1/8"=49.5%. The overall weighted average for Band-Aid bandages with Tear/Cut 3/16"=56%. These percentages illustrate the weighted average of the amount of force required for a user to pull apart a tear vs. the amount of force required for a user to pull apart a cut.

TABLE 2

Separation Force testing of "Nexcare" Brand Bandages

| Model | Size (inch) | Start | Sample size | Average (lbs) | Standard Deviation (lbs) |
| --- | --- | --- | --- | --- | --- |
| Heavy Duty Flex Fabric | 3/4 × 3 | 3/32" * cut | 10 | 9.1 | 1.13 |
| Heavy Duty Flex Fabric | 3/4 × 3 | tear | 30 | 2.7 | 0.71 |
| Comfort Fabric | 3/4 × 3 | 1/8" cut | 10 | 6.7 | 0.91 |
| Comfort Fabric | 3/4 × 3 | tear | 25 | 3.2 | 0.66 |

* border width was not sufficient for 1/8" cut

The average for Nexcare bandages of Tear/Cut 3/32"=63%. The overall weighted average for Nexcare bandages of Tear/Cut 1/8"=48%. These percentages illustrate the weighted average of the amount of force required for a user to pull apart a tear vs. the amount of force required for a user to pull apart a cut.

TABLE 3

Separation Force testing of "Royal" Brand Bandages

| Model | Size (inch) | Start | Sample size | Average (lbs) | Standard Deviation (lbs) |
| --- | --- | --- | --- | --- | --- |
| Flex Fabric | 3/4 × 3 | 1/8" cut | 10 | 1.86 | 0.58 |
| Flex Fabric | 3/4 × 3 | tear | 10 | 1.20 | 0.25 |

The average for Royal bandages with Tear/Cut 1/8"=0.65%. The Tear/Cut ratios below each table show that there is a significant advantage to using a hand tear to start the wrapper separation compared to a cut. This percentage illustrates the weighted average of the amount of force required for a user to pull apart a tear vs. the amount of force required for a user to pull apart a cut.

While specific embodiments have been described above, it will be appreciated that the disclosure may be practiced otherwise than as described. The descriptions above are intended to be illustrative, not limiting. Thus, it will be apparent to one skilled in the art that modifications may be made to the disclosure as described in the foregoing without departing from the scope of the claims set out below.

What is claimed is:

1. A wrapped bandage comprising:
a wrapper including a top portion and a bottom portion, wherein a longitudinal edge is defined by the top and the bottom portions to extend between a first end and a second end of the wrapper, the longitudinal edge being substantially continuous and straight from the first end to the second end;
an elongated bandage contained in the wrapper and including a first pressure sensitive adhesive area on a first end portion of the bandage, a second pressure sensitive adhesive area on a second end portion of the bandage, and a wound dressing pad disposed between the first and the second adhesive areas;
a first cover strip and a second cover strip wherein the cover strips are substantially the same length, the first cover strip has a first protective portion that covers the first adhesive area on the first end portion of the bandage and also covers a portion of the wound dressing pad, and the second cover strip has a second protective portion that covers the second adhesive area on the second end portion of the bandage and also covers a portion of the wound dressing pad;
the first cover strip has a first fold in the region of the wound dressing pad at which a first folded portion of the first cover strip folds back and over the first protective portion, and the second cover strip has a second fold in the region of the wound dressing pad at which a second folded portion of the second cover strip folds back and over the second protective portion;
the first folded portion of the first cover strip is dimensioned so that an end of the first folded portion farthest from the pad extends beyond the first adhesive area on the bandage and is sandwiched between the top portion of the wrapper and the bottom portion of the wrapper at the first end of the wrapper;
the second folded portion of the second cover strip is dimensioned so that an end of the second folded portion farthest from the pad extends beyond the second adhesive area on the bandage and is sandwiched between the top portion of the wrapper and the bottom portion of the wrapper at the second end of the wrapper; and
the top and the bottom portions of the wrapper surround the bandage, the first cover strip, and the second cover strip, so that when the first and the second ends of the wrapper and the sandwiched ends of the folded portions of the cover strips are grasped and separated, the cover strips are peeled from the bandage.

2. A wrapped bandage according to claim 1, wherein the first folded portion of the first cover strip and the second folded portion of the second cover strip overlap one another over the wound dressing pad on the bandage.

3. A wrapped bandage according to claim 1, wherein the first cover strip completely covers the first adhesive area on the bandage, and the second cover strip completely covers the second adhesive area.

4. A wrapped bandage according to claim 1, wherein a portion of the longitudinal edge of the wrapper in the region of the wound dressing pad on the bandage includes a tear mark for indicating a position at which a user makes a tear by hand to facilitate opening the wrapper.

5. A wrapped bandage according to claim 1, wherein a slit or notch is formed in the longitudinal edge of the wrapper in the region of the wound dressing pad on the bandage to facilitate opening the wrapper.

* * * * *